United States Patent [19]
Heinze, III

[11] Patent Number: 5,690,609
[45] Date of Patent: Nov. 25, 1997

[54] COMPOUND ABDOMINAL AND BACK SUPPORT BELT SYSTEM

[76] Inventor: Frank D. Heinze, III, 3090 N. Rio Baya, Indialantic, Fla. 32903

[21] Appl. No.: 645,180

[22] Filed: May 13, 1996

[51] Int. Cl.⁶ ........................................ A61F 5/00
[52] U.S. Cl. .................. 602/19; 2/44; 2/311; 128/96.1; 128/115.1
[58] Field of Search .................. 602/19; 450/155; 2/44, 311, 312, 318; 128/96.1, 112.1, 115.1

[56] References Cited

U.S. PATENT DOCUMENTS

| | | | |
|---|---|---|---|
| 1,992,397 | 2/1935 | Rowley | 128/115.1 X |
| 4,696,291 | 9/1987 | Tyo | 602/19 |
| 4,794,916 | 1/1989 | Porterfield et al. | 602/19 |
| 5,363,863 | 11/1994 | Lelli et al. | 602/19 X |
| 5,433,697 | 7/1995 | Cox | 602/19 |

Primary Examiner—Linda C. Dvorak
Attorney, Agent, or Firm—Charles E. Wands

[57] ABSTRACT

A torso support belt system has individually contoured back and abdominal muscle support pads and an associated multi-belt system. The locations of the abdominal and back support pads around the wearer's body are adjustable, so as to provide contoured support for both the back and abdominal regions of the wearer. The back support pad is contoured to generally conform with the wearer's lower back region, while the abdominal muscle support pads are contoured to generally conform with the wearer's abdominal region. The multi-belt system contains inner and outer belts which are looped through slots in the back support pad and the abdominal muscle support pads in such a manner as to securely fasten the abdominal muscle support pads and the back support pad about the torso of the wearer.

23 Claims, 5 Drawing Sheets

COMPOUND ABDOMINAL AND BACK SUPPORT BELT SYSTEM

FIELD OF THE INVENTION

The present invention relates in general to orthopaedic support devices, and is particularly directed to a new and improved torso support belt system, such as may be worn by bodybuilders, for providing adjustable, contoured support for back and abdominal regions of the wearer.

BACKGROUND OF THE INVENTION

Orthopaedic torso support devices currently used by individuals carrying out physical tasks, such as lifting heavy objects, that may subject the torso area of the person's body to substantial stress and strain, are typically of one of two types. The first type, which has a generally flexible configuration, is made of a thin flexible (nylon) sleeve surrounding a flat plastic insert, and is wrapped around the user and joined together by way of respective hook and loop fastener elements. The second type has a relatively inflexible or stiff configuration, and is made of a continuous piece of relatively thick leather, which is buckled in the front of the wearer. Because the former belt is thin and flexible, it provides very little, if any, lower back muscle and spine support, and no abdominal support whatsoever. The leather belt, on the other hand, being relatively stiff, does not readily conform with the contour of the wearer's back and therefore is capable of providing only a limited degree of back support. Also, like the nylon belt, the leather belt offers no abdominal support, having only a pair of straps that are joined together by a buckle fastener in front of the wearer.

SUMMARY OF THE INVENTION

In accordance with the present invention, the above-described shortcomings of conventional torso belts are effectively overcome by an orthopaedic torso support belt system, that has individually contoured back and abdominal support pad components, whose relative locations around the wearer's body are adjustable, so as to provide contoured support for both the back and abdominal regions of the wearer. For this purpose, the torso support belt system of the present invention includes a back support pad, a pair of abdominal muscle support pads, and an associated multi-belt system. The back support pad is contoured to generally conform with the wearer's lower back region, while the abdominal muscle support pads are contoured to generally conform with the wearer's abdominal region. The multi-belt system contains inner and outer belts which are looped through slots in the back support pad and the abdominal muscle support pads, in such a manner as to securely fasten the abdominal support pads and the back support pad about the torso of the wearer. In effect, the torso belt system of the present invention provides an exoskeleton-type of support for the wearer's torso.

The back support pad has a curvilinear perimeter, that is defined by a slightly curved or straight upper edge portion, an undulating bottom edge portion, and first and second side edge portions. The back support pad itself is comprised of a laminate structure formed of a first sheet of contoured plastic and cushion layer of closed cell plastic foam. The sheet of contoured plastic of the back support pad is slightly flexible, rather than being inflexibly rigid, so that it can 'give' somewhat while providing firm, yet comfortable lower back support, when secured against the waist region of lower back of the wearer. The interior cushion layer serves to make the pad fit comfortably to the wearer when the belt is cinched to a snug fit.

The back support pad is sized and shaped to extend generally the width of the wearer's back region on either side of the spine to a position along the waistline such that the side edge portions of the back support pad will slightly 'wrap' around the lower back region of the wearer, so as to provide comfortable, yet protective, lower back support, when the torso belt system is drawn to a snug fit about the wearer.

The upper edge portion of the back support pad is contoured slightly outwardly or away from the waist centerline so that the upper edge portion is not uncomfortably rigid against the wearer, but allows some freedom of movement, for example permitting the wearer to bend or squat. The undulating shape of the bottom edge of the back support pad includes a recess that accommodates the area of the tailbone or coccyx between a pair of generally convex regions on either side of the recess. Like the upper edge of the back support pad, its lower edge is contoured slightly away from the waist centerline so that the lower edge is not uncomfortably rigid against the upper hip region, thereby affording freedom of movement of the wearer, while supporting the lower back.

The back support pad engages the inner belt and the outer belt of the dual belt by means of a pair of generally longitudinal slots therethrough, which are sized to receive doubled sections of the inner belt. For ease of adjustment, the inner belt is preferably made of elastic material, and is looped upon and joined to itself along the exterior face of the back support pad. Each of these longitudinal slots is also sized and configured to allow passage therethrough of the outer belt which overlies the inner belt and passes through a further pair of slots in the back support pad that are spaced apart from respective slots.

The right and left abdominal support pads are configured to be joined together into a unitary abdominal support pad structure that generally conforms with a wearer's abdominal region. Like the back support pad, the abdominal support pads are shaped to have a generally curvilinear perimeter defined by generally straight upper and lower edges and first and second side edges. Like the back support pad each of the abdominal support pads is comprised of a laminate structure of a sheet of contoured plastic, and a closed cell foam cushion layer.

The right abdominal support pad is dimensioned to extend across the right side of the abdominal region of the wearer and to be overlapped along its left side edge by the right side edge of the left abdominal support pad. Similarly, the left abdominal support pad is dimensioned to extend across the left side of the abdominal region of the wearer, with its right side edge overlapping the left side edge of the right abdominal support pad.

In the area of overlap of the respective right and left abdominal support pads, complementary attachment elements, such as respective strips or patches of hook and loop fastener material are adhered to mutually facing sides of the right and left side abdominal support pads. When joined together the two abdominal support pads have an effective width that extend across the entirety of the abdominal region of the wearer, so as to provide full abdominal region support.

In order to accommodate each of the inner belt and the outer belt of the dual belt system, the abdominal support pads have generally longitudinal slots which are sized to allow passage therethrough of looped portions of the inner belt, so that the inner belt may be looped around side edge portions of the abdominal support pads. The abdominal pads further include additional slots, so that the outer belt passes through both sets of slots. Adjacent to free ends of the outer belt are strips of hook and loop fastener material that are configured to engage complementary loop and hook strips on the outer surface of the outer belt at the sides of the wearer's waist.

Once the inner and outer belts of the orthopaedic torso support belt system of the present invention are looped through the longitudinal slots in the back support pad and the abdominal support pads, the belt may be placed about the waist of the wearer, the abdominal pads joined together by the loop and hook fasteners, and the outer belt cinched snug, so as to securely fasten the abdominal support pads and the back support pad about the torso of the wearer. To take off the torso belt, the wearer simply pulls the free ends of the outer belt away from the loop and hook fastener strips on the outer belt at the sides of the wearer's waist, so as to release the belt-tightening action against the pads. One of the free ends of the outer belt is then pulled completely through a buckle so that the free ends of the outer belt may be fully separated from one another. The user then unclasps the (hook and loop) fastener elements in the overlap area of the abdominal support pads from each other, thereby fully opening the torso belt system, allowing it is removal from about the wearer's waist.

In order to reduce both processing complexity and cost, the present invention employs a relatively simplified manufacturing technique for forming the compound curved back support and abdominal support pads. According to this process, a laminate of generally flat sheets of plastic material and closed cell foam adhesively bonded thereto are subjected to a pad severing operation. In this step, respective pads corresponding to those of the back support pad and the pair of abdominal support pads are severed from the laminate, preferably by die-cutting, which both forms the longitudinal slots and removes cut-out portions from the laminate.

The removed pad portions are then heated to a temperature which makes the plastic material sufficiently pliable to allow its shape to be modified by a mold into a compound curve, and so that, when cooled, the molded plastic pads will retain the intended compound curve shape. The pliable pads are then placed upon molds which conform with the intended compound curve shapes of the back support and abdominal support pads. In this step, the hook and loop fastener patches with their adhesive backing may be placed upon the abdominal support pads in the area of overlap.

Respective frames to which webs of elastic material, such as latex rubber, are pulled down atop each mold. As the latex rubber webbing layers are pulled down atop the plastic and molds, they apply a mold-conforming pressure to the die-cut pliable portions of the generally flat sheet of plastic as placed upon the molds, which causes the pliable portions of the removed portions of the die-cut plastic to conform with the shape of the molds and thereby assume their compound contours. This pressure is also applied to the adhesive material regions of the hook and loop fastener elements so as to secure these elements to the abdominal pads. With the latex rubber webbing pulled down around the molds, the frames may be clamped in place upon underlying frame support member, and the plastic pads allowed to cool.

After the plastic pads have cooled, the frames are rotated away from the molds and the pads are removed. Each die-cut portion of the originally generally flat sheet of pad laminate will have conformed with the shape of its associated mold and will thereby assume its intended multi-dimensional contour for abdominal or back support. The pads can now be assembled into a complete belt system, by looping respective inner and outer belts through the slots of the pads.

DETAILED DESCRIPTION

As pointed out briefly above, the orthopaedic torso support belt system according to the present invention is configured to provide adjustable, contoured support for both the back and abdominal regions of the wearer. For this purpose, as illustrated in the perspective view of FIG. 1, the torso support belt includes a back support pad 10, having a compound curve contour which generally conforms with the wearer's lower back region, and a pair of abdominal muscle support pads 20 and 30 that are contoured to generally conform with a wearer's abdominal region. The abdominal support pads 20 and 30 are joined to the back support pad 10 by a dual belt system 40 comprised of and inner belt 50 and an outer belt 60. As will be described, the inner and outer belts are looped through each of the back support pad 10 and abdominal muscle support pads 20 and 30 in such a manner as to securely fasten the abdominal muscle support pads and the back support pad about the torso of the wearer.

Figure 2:
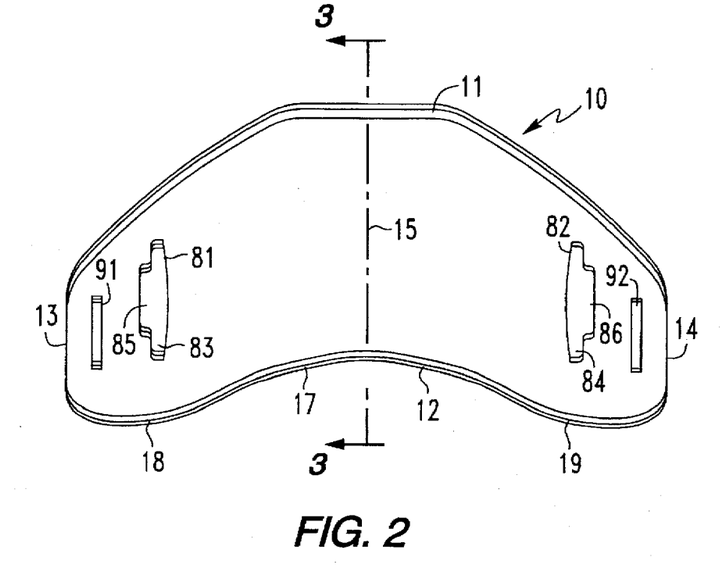
FIG. 2 is a front view of the configuration of a back support pad.
Figure 3:
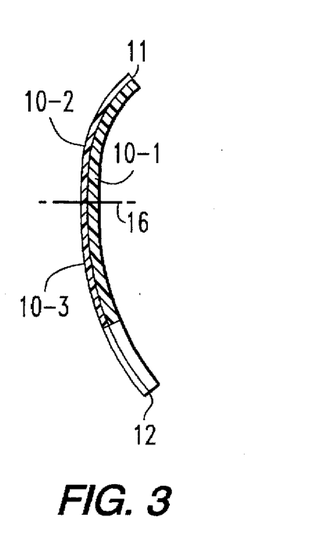
FIG. 3 is a cross-sectional side views of a back support pad taken along lines 3—3 in FIG. 2.

Referring now to the front and cross-sectional side views of FIGS. 2 and 3, respectively, the configuration of the back support pad 10 is diagrammatically illustrated as having a curvilinear perimeter, that is defined by a slightly curved or straight upper edge portion 11, an undulating bottom edge portion 12, and first and second side edge portions 13 and 14, respectively which adjoin the top edge portion 11 and the lower edge portion 12. The back support pad itself is comprised of a laminate structure having a first sheet of contoured plastic 10-1, such as a sheet of contoured Kydex 100 plastic, having a thickness on the order of an eighth of an inch, as a non-limiting example. Advantageously, such a material is somewhat flexible, rather than being inflexibly rigid, so that it can 'give' somewhat while providing firm, yet comfortable lower back support, when secured against the back of the wearer. To complete the laminate structure of the back support pad 10, a second, generally flexible cushion layer 10-2, such as a layer of closed cell plastic foam material, is affixed (e.g., glued) to an interior (back-facing) surface 10-3 of the contoured plastic sheet 10-1.

Because the first sheet of contoured plastic 10-1 is somewhat flexible it provides firm lower back support, when secured against the waist region of lower back of the wearer. The interior cushion layer 10-2 serves to provide sufficient comfort to the wearer when the belt is cinched to a snug fit. In order to conform with the lower back region, while still affording freedom of movement of the wearer, the back support pad 10 has a three dimensional or compound, back-conformal contour. In addition, the back support pad 10 is sized and shaped to slightly extend generally the width of the wearer's back region on either side of a vertical or spine centerline 15, to a position along a horizontal or waist centerline 16, such that the first and second side edge portions 13 and 14 of the back support pad 10 will slightly 'wrap' around the waist region of the lower back of the wearer, so as to provide comfortable, yet protective, lower back support, when the torso belt is snugly cinched around the wearer. The upper edge portion 11 of the back support pad 10, which is dimensioned to extend partially across the lower back on either side of the spine centerline 15, is contoured slightly outwardly or away from the waist centerline 16, so that the upper edge portion 11 is not uncomfortably rigid against the wearer, but allows some freedom of movement, for example to permit the wearer to bend or squat.

The undulating shape of the bottom edge portion 12 of the back support pad 10 across its width includes a recess or concave portion 17 that provides sufficient room for the tailbone or coccyx between a pair of generally convex regions 18 and 19 on either side of the recess 17. Like the upper edge portion 11 of the back support pad 10, its lower edge portion 12, which is dimensioned to extend partially across the upper hip region on either side of the spine centerline 15, is contoured slightly outwardly or away from the waist centerline 16, so that the lower edge portion 12 of the back support pad 10 is not uncomfortably rigid against the upper hip region, so as to simultaneously afford freedom of movement of the wearer, while supporting the lower back.

In order to accommodate each of the inner belt 50 and the outer belt 60 of the dual belt system 40, the back support pad 10 has a pair of first, generally longitudinal slots or openings 81 and 82, which are sized to allow passage therethrough of adjacent or doubled sections of the inner belt 50 sections, so that the inner belt 50 may be looped upon and joined to itself along the exterior face of the back support pad, as will be described. Each of slots 81 and 82 is also sized and configured to allow passage therethrough of the outer belt 60, which overlies the inner belt 50 and passes through a further pair of slots or openings 91 and 92 in the back support pad 10, that are spaced apart from respective slots 81 and 82.

For this purpose, slots 81 and 82 have first, relatively wide portions 83 and 84, and second, relatively narrow portions 85 and 86, contiguous therewith. The differential widths of the relatively wide portions 83 and 84 and the relatively narrow portions 85 and 86 of the slots are for the purpose of accommodating different belt widths for the belts 50 and 60. As a non-limiting example, the inner belt 50, which is preferably made of elastic material to facilitate adjustment of the torso belt, as described previously, may be dimensionally wider (and thinner) than the outer belt 60, and passes through the relatively wide portions 83 and 84 of slots 81 and 82. Namely, the relatively wider portions 83 and 84 of slots 81 and 82 allow the (wider) inner belt 50 to be looped upon and joined to itself along the exterior face 10-4 of the back support pad 10, as diagrammatically illustrated at 51 and 52 in the plan view of FIG. 4. The relatively narrower portions 85 and 86 of slots 81 and 82 are sized to receive the (narrower) outer belt 60, which also passes through slots 91 and 92.

Figure 5:
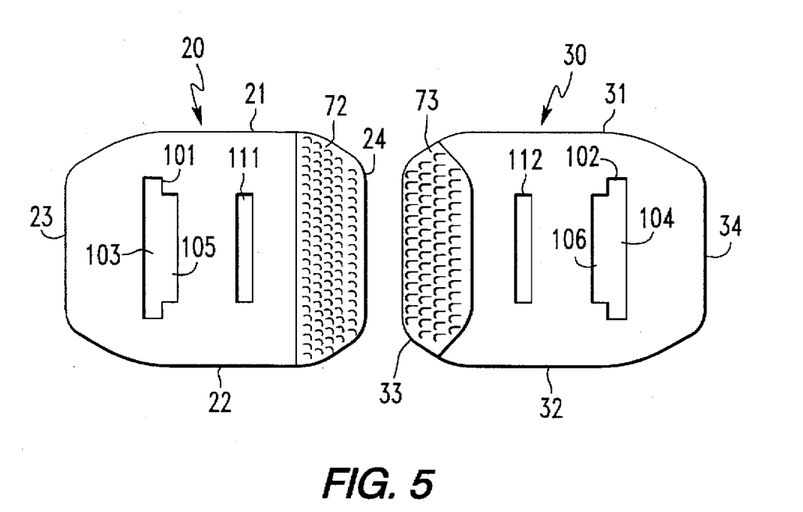
FIG. 5 is a front view of the configuration of respective right and left side abdominal support pads.
Figure 6:
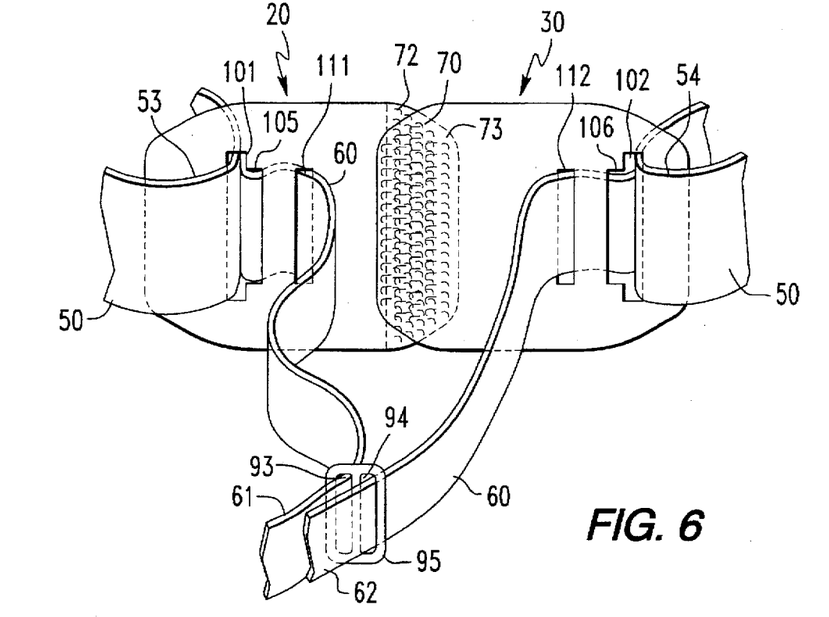
FIG. 6 is a front view of an overlapped condition of right and left side abdominal support pads.

The respective right and left abdominal support pads 20 and 30, which are configured to be joined together into a unitary support pad structure that generally conforms with a wearer's abdominal region, are shown in detail in FIGS. 5 and 6. Similar to the back support pad 10, described above, the right abdominal support pad 20 is shaped to have a generally curvilinear perimeter that is defined by generally straight upper and lower edge portions 21 and 22, respectively, and first and second side edge portions 23 and 24, which adjoin the top edge portion 21 and the lower edge portion 22. Likewise, the left abdominal support pad 30 has a generally curvilinear perimeter that is defined by generally straight upper and lower edge portions 31 and 32, respectively, and first and second side edge portions 33 and 34, which adjoin the top edge portion 31 and the lower edge portion 32.

Like the back support pad 10, each of the right and left abdominal support pads 20 and 30 is comprised of a laminate structure having a first, generally inflexible sheet of contoured plastic, such as the above-referenced Kydex 100 plastic material, and a second, generally flexible closed cell foam cushion layer affixed to an interior surface of the contoured plastic sheet, thereby providing firm, yet comfortable abdominal region support, when the belt is cinched to a snug fit.

The right abdominal support pad 20 is dimensioned to extend across the right side of the abdominal region of the wearer and to be overlapped along its side edge 24 by the side edge 33 of the left abdominal support pad 30. Similarly, the left abdominal support pad 30 is dimensioned to extend across the left side of the abdominal region of the wearer, with its side edge 33 overlapping the side edge 24 of the right abdominal support pad 30.

As shown in FIG. 6, in the area of overlap 70 of mutually opposing faces of the respective right and left abdominal support pads 20 and 30, an attachment element 72, such as a piece of hook/loop fastener material is adhered to the interior (or exterior) face of the right side abdominal support pad 20. In a complementary fashion, in this area of abdominal support pad, an attachment element 73, such as a piece of loop/hook fastener material, that readily attaches itself to the attachment element 72 of the right side abdominal support pad 20, is adhered to the exterior (or interior) face of the left side abdominal support pad 30. When joined together as shown in FIG. 6, the two abdominal support pads 20 and 30 have an effective width that extend across the entirety of the abdominal region of the wearer, so as to provide full abdominal muscle support.

In order to accommodate each of the inner belt 50 and the outer belt 60 of the dual belt system 40, the abdominal support pads 20 and 30 have first, generally longitudinal slots or openings 101 and 102 therein. Like slots 81 and 82 in the back support pad 10, the slots 101 and 102 in the respective abdominal support pads 20 and 30 have first, relatively wide portions 103 and 104, and second, relatively narrow portions 105 and 106, contiguous therewith. Spaced apart from the slots 101 and 102 are further slots or openings 111 and 112 in the respective abdominal support pads 20 and 30.

Figure 1:
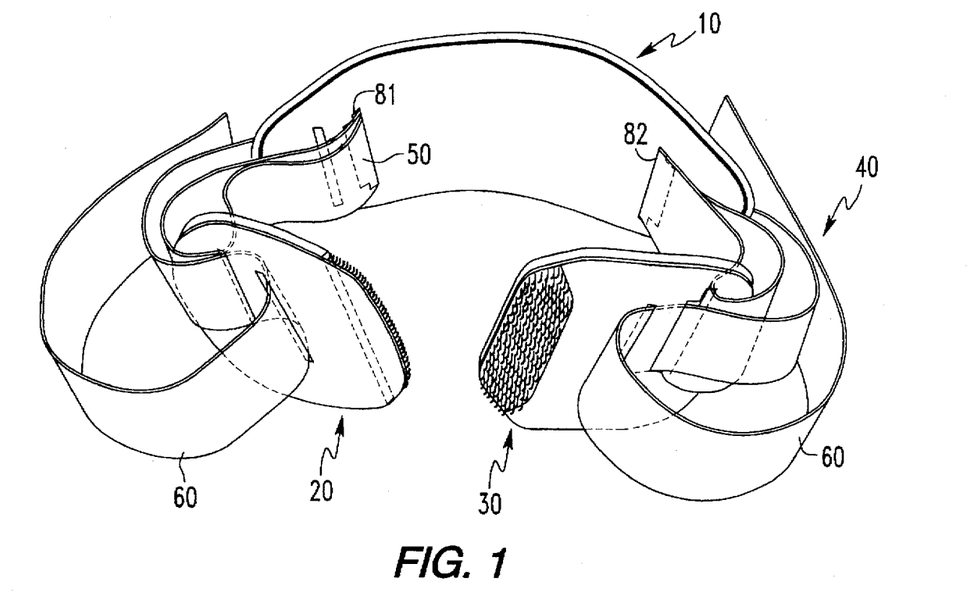
FIG. 1 is a perspective view of the torso support belt system of the present invention.
Figure 4:
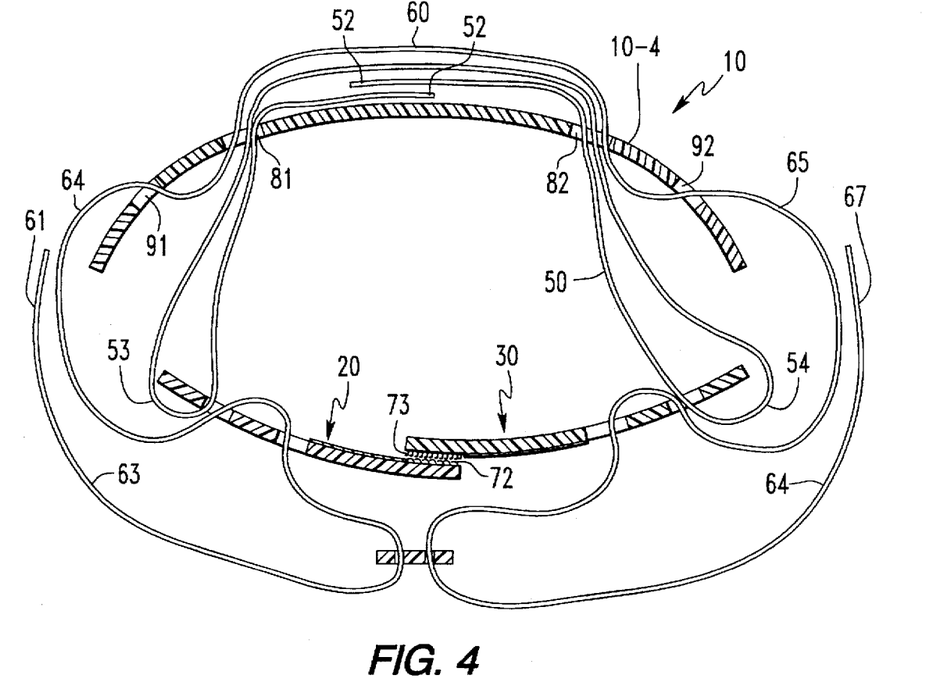
FIG. 4 is a plan view of the torso support belt system of the present invention.

As diagrammatically illustrated in FIGS. 1 and 6 and in the plan view of FIG. 4, the relatively wide portions 103 and 104 of respective slots 101 and 102 are sized to allow passage therethrough of looped portions 53 and 54 of the inner belt 50 sections, so that the inner belt 50 may be looped around side edge portions 24 and 34 of the abdominal support pads 20 and 30, respectively. The relatively narrow portions 105 and 106 of respective slots 101 and 102 are sized to receive the (narrower) outer belt 60, which also passes through slots 111 and 112. Extending along either sides of the outer belt from the free ends 61 and 62 thereof are strips of fastening material, such as hook and loop material 63 and 64. These fastener strips 63 and 64 are configured to engage complementary fastener strips, such as strips 65 and 66 of loop and hook material on the outer surface of belt 60 at the sides of the wearer's waist.

Figure 7:
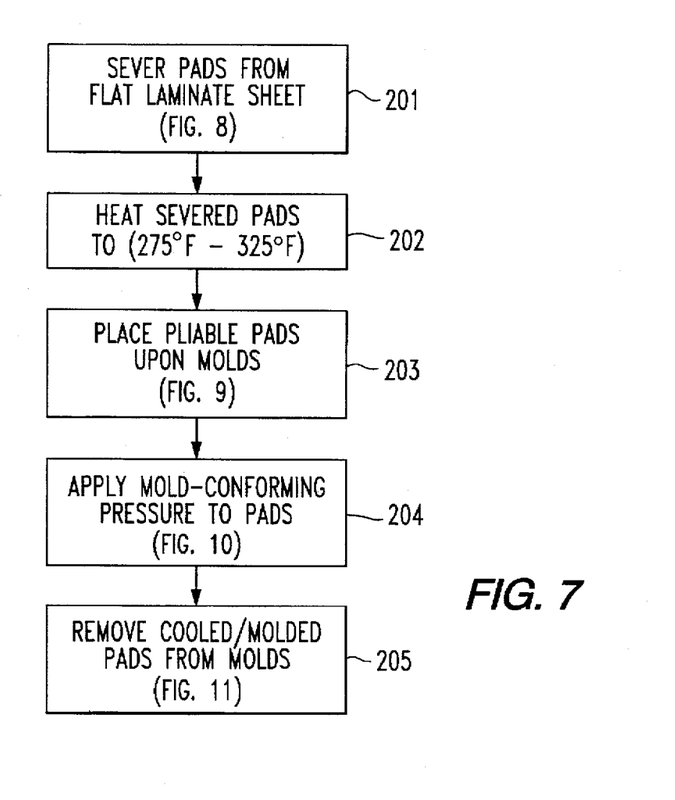
FIG. 7 is a flow chart associated with the manufacturing process for forming the compound curved back support and abdominal support pads of the torso support belt system of the present invention.
Figure 8:
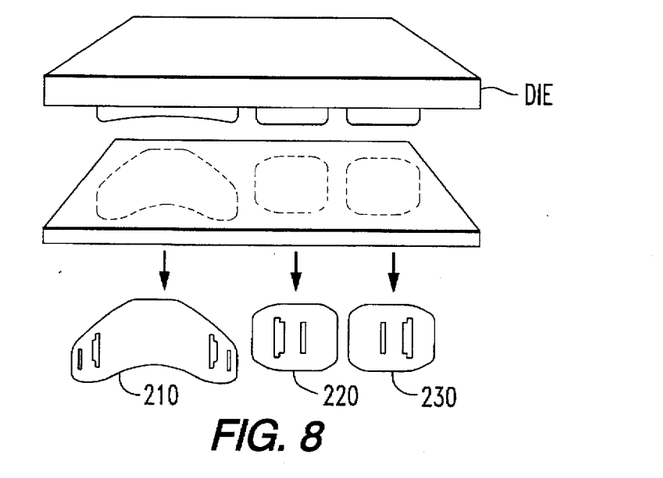
FIGS. 8–11 show the use of a molding apparatus for forming the compound curved back support and abdominal support pads of the torso support belt system of the present invention.

With the respective inner and outer belts 50 and 60 of the orthopaedic torso support belt according to the present invention looped through the longitudinal openings in the back support pad 10 and abdominal muscle support pads 20 and 30, as shown in FIGS. 1 and 7, the belt may be placed about the waist of the wearer and the outer belt cinched snug, so as to securely fasten the abdominal muscle support pads and the back support pad about the torso of the wearer.

For this purpose, the user grasps the abdominal muscle support pads 20 and 30, which are captured on the inner elastic belt 50 at looped portions 53 and 54 thereof, as described above. With the back support pad 10 placed against the wearer's lower back region, the two abdominal pads and attached belt system 40 are wrapped around the waist are of the wearer, and the abdominal pads 20 and 30 brought together and joined in the area of the wearer's abdominal region by way of the (loop and hook) fastener elements 72 and 73, described above. Because the inner belt 50 is made of elastic material, the wearer can adjust the abdominal pads as desired for full, yet comfortable, abdominal support.

Next, as shown in FIG. 6, free ends 61 and 62 of the outer belt are then passed through slots or openings 93, 94 in a buckle 95. The wearer may then cinch the outer belt down, by pulling on the free ends 61 and 62, to draw the side edge portions 23 and 34 of the abdominal support pads 20 and 30, respectively, toward the side edge portions 13 and 14 of the back support belt 10. Since the side edge portions 24 and 33 of the abdominal support pads 20 and 30 are attached by the hook and loop fasteners 72 and 73 at overlap area 70, the effect of cinching down the outer belt 60 and thereby drawing the side edge portions of the abdominal support pads 20 and 30, toward the side edge portions of the back support belt 10 is to fit the entire belt system snugly against the wearer, with the joined-together abdominal pads 20 and 30 providing abdominal muscle support and with back support pad providing lower back support.

The free ends 61 and 62 are then held in place against the outer belt 60 be placing the strips 63 and 64 of hook and loop fastener material against the complementary loop and hook fastener strips 65 and 66 on the outer surface of belt 60 at the sides of the wearer's waist. In this wrapped-around and cinched-down condition, the torso belt system of the present invention is now retained firmly in place about the wearer's waist. The joined-together abdominal pads in the front of the wearer's torso support the abdominal muscle region, and the back support pad being comfortably held in place against the wearer's lower back provides lower back support.

To take off the torso belt, the wearer simply pulls the free ends 61 and 62 of the outer belt away from the loop and hook fastener strips 65 and 66 on the outer surface of belt 60 at the sides of the wearer's waist, so as to release the belt-tightening action against the pads. One of the free ends 61 and 62 of the outer belt 60 is then pulled completely through the buckle 95, so that the free ends of the outer belt may be fully separated from one another. The user then unclasps the (hook and loop) fastener elements 72 and 73 in the overlap area 70 of the abdominal muscle support pads 20 and 30 from each other, thereby fully opening the torso belt system, allowing it is removal from about the wearer's waist.

As pointed out above, in order to reduce both processing complexity and cost, the present invention employs a relatively simplified manufacturing process for forming the compound curved back support and abdominal support pads, the steps of which are listed in the flow chart of FIG. 7, with associated conditions of the pads diagrammatically illustrated in FIGS. 8–11.

Pursuant to the first step in the process, shown at step 201 in FIG. 7, a laminate of generally flat sheets of plastic material, such as sheet of the above-referenced textured Kydex 100 plastic having a thickness on the order of an eighth of an inch, as described above, and the closed cell foam adhesively bonded thereto, are subjected to a pad severing operation. In this step, respective pads corresponding to those of the back support pad 10, and the pair of abdominal support pads 20 and 30, described above and shown in FIG. 8, are severed from the laminate, preferably by die-cutting, which both forms the longitudinal slots and removes cut-out portions 210, 220 and 230 from the laminate.

Next, at step 202, the cut-out or severed portions 210, 220 and 230 of the laminate are heated to a temperature which makes the plastic material sufficiently soft or pliable to allow its shape to be modified into a compound curve, so that when cooled the plastic will retain the intended compound curve shape. For this purpose, the severed plastic pads may be heated to a temperature on the order of 275° F.–325° F. A conventional industrial electric convection-heating plate may be used for this purpose.

Figure 9:
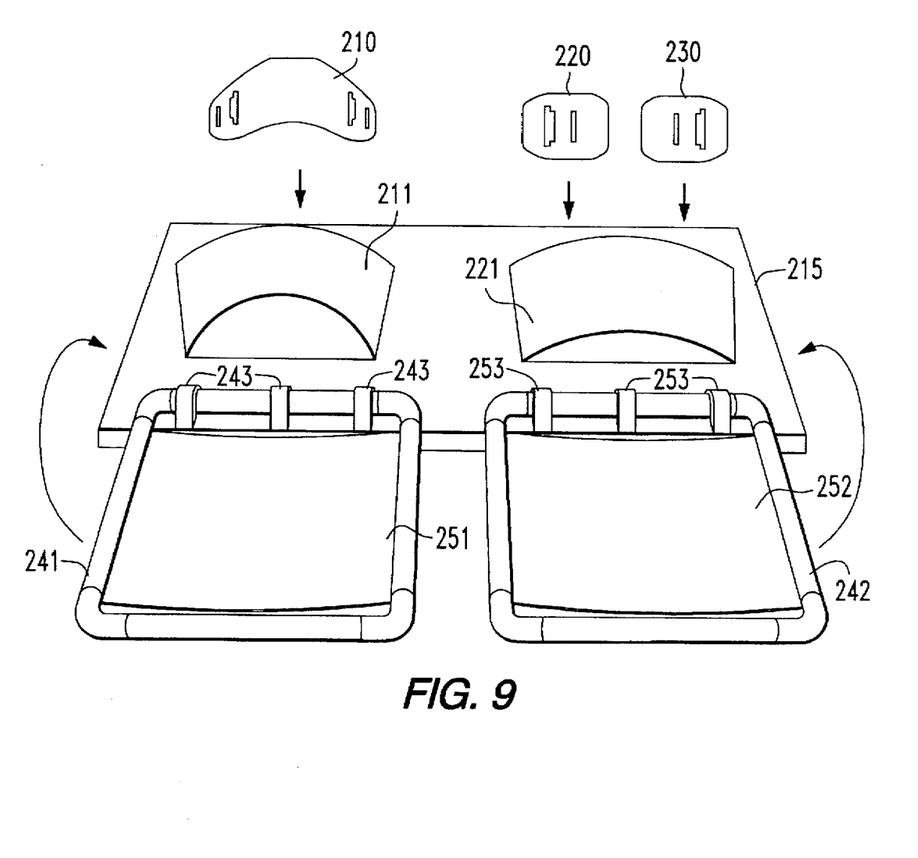
Figure 10:
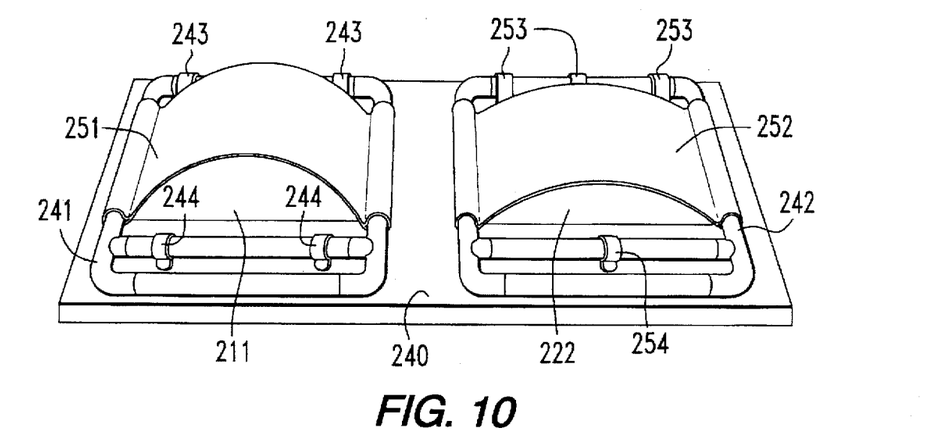

In step 203, the pliable back support pad laminate portion 210 is then placed upon a mold, such as a plaster of paris mold, that is coated with a smoothing material such as a nylon net material or the like, as a non-limiting example, shown at 211 in FIG. 9, which conforms with the intended compound curve shape of the back support pad 10. Similarly, the pliable abdominal support pad cut-out portions 220 and 230 are placed at adjacent locations of a mold 221, whose surface shape conforms with the intended compound curve shapes of the abdominal support pads 20 and 30. If desired, during this step, adhesively backed strips or patches 72 and 73 of hook and loop fastener material may be placed on the pad portions 220 and 230. Alternatively, they may be applied to the pads 20 and 30 after the molding process.

With the pad cut-out portions 210, 220 and 230 situated upon the two molds 211 and 221, in step 204, respective frames 241 and 242, such as frames of PVC pipe, to which webs of elastic material 251 and 252, such as one-sixteenth inch thick sections of latex rubber, are attached, are rotated about support fixtures 243 and 253 mounted to an underlying substrate 215 and pulled down atop each mold. As the frames 241 and 242, and the latex rubber webbing layers 251 and 252 affixed thereto are pulled down atop the plastic laminate cut-outs and the molds therebeneath, they apply a mold-conforming pressure to the die-cut pliable pad portions 210, 220 and 230, which causes the pliable portions of the removed portions of the die-cut plastic to take on or conform with the shape of the molds and thereby assume their compound contours.

This pressure is also applied to the adhesive material of hook and loop fastener elements 72 and 73 that has been attached to the abdominal support laminate cut-outs 220 and 230, so as to secure these fastener elements to the abdominal pads 20 and 30. With the latex rubber webbing pulled down around the molds, the frames 241 and 242 may be clamped in place upon underlying frame support member 240, as shown at 244 and 254 in FIG. 10, and the plastic pads allowed to cool. To assist in gradual cooling, a fan may be used to blow room temperature air across the molds.

Figure 11:
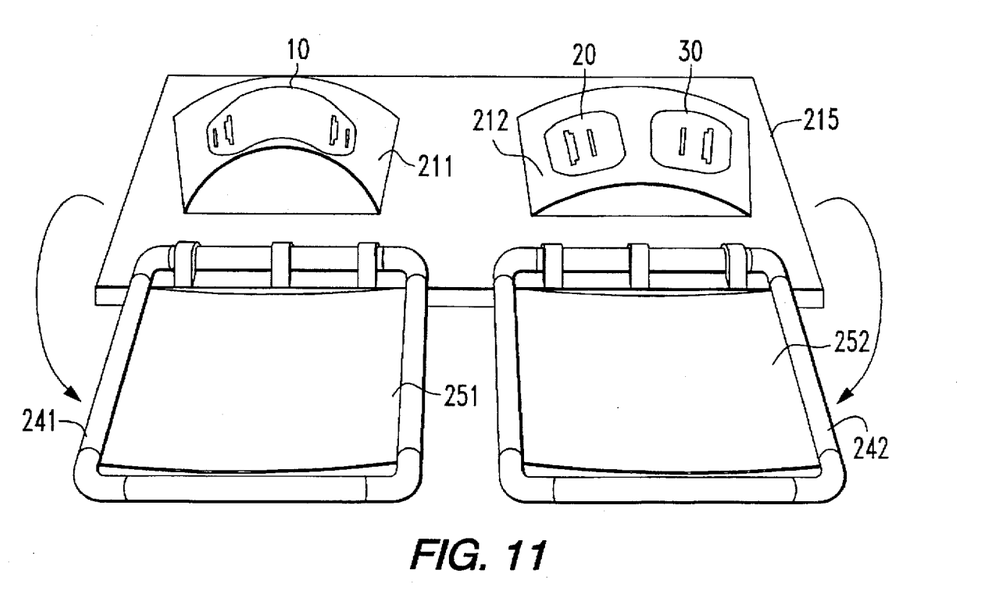

Once the plastic pads have cooled sufficiently to retain the shapes imparted by the molds (for example to a temperature on the order of 160° F.–180° F. and preferably room temperature), to facilitate handling, at step 205, the frames 241 and 242 are rotated away from the molds 211 and 212, and the pads 10, 20 and 30 are removed, as shown in FIG. 11. Each molded die-cut portion of the originally generally flat sheet of plastic will have conformed with the shape of its associated mold (211 or 212) and will thereby assume its intended multi-dimensional back or abdominal support contour of its associated mold. The pads can now be assembled into a complete belt system, by looping respective inner and outer belts 50 and 60 through the slots of the pads, as described above.

As will be appreciated from the foregoing description, the shortcomings of conventional bodybuilder belts, such as the nylon and leather configurations, described previously, are effectively overcome by the torso support belt system of the present invention, which has individually contoured back and abdominal region support pad components. The back support pad is contoured to generally conform with the wearer's lower back region, while the abdominal region support pads are contoured to generally conform with the wearer's abdominal region. Advantageously, with the adjustable belt system of the present invention, the locations of the abdominal and back support pads around the wearer's body may be placed as desired by the wearer, so as to provide what is effectively akin to an exoskeleton-type of back and abdominal support for the wearer's torso.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein, but intend to cover all such changes and modifications as are obvious to one of ordinary skill in the art.

What is claimed:

1. A torso support apparatus comprising:
   a back support pad that is contoured to generally conform with a wearer's lower back region;
   a plurality of abdominal muscle support pads configured to engage one another to form an abdominal muscle support structure for a wearer's abdominal muscle region, and contoured to generally conform with said wearer's abdominal muscle region;
   an inner, elastic belt structure, which is arranged to extend around the sides of the torso of said wearer, and elastically positions said plurality of abdominal muscle support pads in spaced apart relationship to said back support pad, so as to form therewith a compound torso support structure that includes said abdominal muscle support structure, said inner, elastic belt and said back support pad; and
   an outer belt structure, which engages said plurality of abdominal muscle support pads and said back support pad of said compound torso support structure, is arranged outside of said inner, elastic belt structure, and is operative to tighten said abdominal muscle support structure and said back support pad about the torso of the wearer, causing a reduction in tension of said inner, elastic belt structure, and maintaining said abdominal muscle support structure supporting said wearer's abdominal muscle region and said back support pad supporting said wearer's lower back region.

2. A torso support apparatus according to claim 1, wherein each of said back support pad and said plurality of abdominal muscle support pads is comprised of a laminate structure having a first, generally inflexible contoured torso support member laminate with a second, generally flexible cushion member adjacent thereto.

3. A torso support apparatus according to claim 1, wherein each of said abdominal muscle support pads has a first opening therein, through which a respective looped portion of said inner, elastic belt structure passes, and wherein said back support pad has a pair of first openings therein, through which respective portions of said inner, elastic belt structure that extend to looped portions thereof pass, for attaching said plurality of abdominal muscle support pads in spaced apart relationship to said back support pad.

4. A torso support apparatus according to claim 3, wherein said inner, elastic belt structure has first and second ends, which pass through respective ones of said pair of first openings in said back support pad, and are joined together to form said inner, elastic belt structure into a continuous loop configuration that attaches said plurality of abdominal muscle support pads in spaced apart relationship to said back support pad.

5. A torso support apparatus according to claim 3, wherein said back support pad has a pair of second openings therein, each of said abdominal support pads has a second opening therein, and wherein said outer belt structure passes through said first and second openings in said back support pad and said first and second openings in said abdominal muscle support pads in such a manner as to tighten said plurality of abdominal muscle support pads and said back support pad about the torso of the wearer.

6. A torso support apparatus according to claim 5, further including a belt loop element through which respective ends of said outer belt structure, that have passed through said first and second openings in said abdominal muscle support pads, pass and allow said respective ends of said outer belt structure to be looped back upon and engage portions of said outer belt structure between said back support pad and said pair of abdominal support pads.

7. A torso support apparatus according to claim 6, wherein said respective ends of said outer belt structure are configured to be joined to said portions of said outer belt structure between said back support pad and said pair of abdominal support pads.

8. A torso support apparatus according to claim 7, wherein said respective ends of said outer belt structure include fastener elements which are joined to associated fastener elements provided at said portions of said outer belt structure between said back support pad and said pair of abdominal support pads.

9. A torso support apparatus according to claim 8, wherein adjacent portions of said plurality of abdominal muscle support pads include fastener elements that are configured to be joined together so as to form said plurality of abdominal muscle support pads into said abdominal muscle support structure.

10. A torso support apparatus according to claim 9, wherein each of said back support pad and said plurality of abdominal muscle support pads is comprised of a laminate structure having a first, generally inflexible contoured torso support member laminate with a second, generally flexible cushion member adjacent thereto.

11. A torso support belt comprising a back support pad and a plurality of abdominal muscle support pads, whose relative locations around a wearer's body are adjustable by means of a multi-belt system, said back support pad being contoured to generally conform with the wearer's lower back region, and said plurality of abdominal muscle support pads being contoured to generally conform with the wearer's abdominal muscle region, and wherein said multi-belt system includes an inner, elastic belt, and an outer belt, which are looped through slots in said back support pad and said abdominal muscle support pads in such a manner as to securely fasten said abdominal muscle support pads and said back support pad about the torso of the wearer, said outer belt extending outside of said inner, elastic belt and, upon being tightened, causing a reduction in tension of said inner, elastic belt, while maintaining said abdominal muscle support pads supporting said wearer's abdominal muscle region, and said back support pad supporting said wearer's lower back region.

12. A torso support belt according to claim 11, wherein said back support pad has a curvilinear perimeter, that is defined by an upper edge portion, an undulating bottom edge portion, and first and second side edge portions, and is comprised of a laminate structure of a sheet of contoured plastic and a cushioning layer, and is sized and shaped to slightly extend generally the width of the wearer's back region on either side of a spine centerline to a position along a waist centerline, such that the side edge portions of the back support pad will slightly wrap around the waist region of the lower back of the wearer, so as to provide protective, lower back support when the torso belt is snugly attached around the wearer.

13. A torso support belt according to claim 12, wherein said upper edge portion of the back support pad is contoured slightly outwardly from the waist centerline so that the upper edge portion is not rigid against the wearer, but allows freedom of movement, and wherein said undulating shape of the bottom edge of the back support pad includes a recess that accommodates the area of the coccyx between a pair of generally convex regions on either side of the recess, and is contoured away from the waist centerline so that the lower edge is not rigid against the upper hip region, thereby affording freedom of movement of the wearer, while supporting the lower back.

14. A torso support belt according to claim 13, wherein said back support pad engages said inner belt and said outer belt of said multi-belt system by means of longitudinal slots which are sized to receive doubled sections of the inner belt so that the inner belt may be looped upon and joined to itself along an exterior face of said back support pad, and wherein each of said slots is configured to allow passage therethrough of said outer belt which passes through a further pair of slots in said back support pad that are spaced apart from said longitudinal slots.

15. A torso support belt according to claim 14, wherein said inner belt is looped upon and joined to itself along said exterior face of said back support pad.

16. A torso support belt according to claim 11, wherein said abdominal support pads are configured to be joined together into a unitary support pad structure that generally conforms with a wearer's abdominal muscle region, and include a right abdominal support pad that is sized to extend across the right side of the abdominal muscle region of the wearer and is overlapped with and attached to a left abdominal support pad that is sized to extend across the left side of the abdominal muscle region of the wearer.

17. A torso support belt according to claim 16, wherein a respective abdominal support pad has a curvilinear perimeter, that is defined by an upper edge portion, a bottom edge portion, and first and second side edge portions, is comprised of a laminate structure of a sheet of contoured plastic and a cushioning layer, and is sized and shaped to extend over a portion of the wearer's abdominal region, such that when the abdominal support pads are joined together, and the torso support belt is snug around the wearer, the joined-together abdominal support pads provide protective, abdominal muscle support.

18. A torso support belt according to claim 17, wherein said abdominal support pads engaged said inner belt and said outer belt of said multi-belt system by means of longitudinal slots therein, which are sized to receive said inner belt so that the inner belt may be looped upon and joined to itself, and wherein each of said slots is configured to allow passage therethrough of said outer belt, which also passes through additional slots in respective abdominal support pads spaced apart from the longitudinal slots therein.

19. A torso support apparatus comprising:

a back support pad that is contoured to generally conform with a wearer's lower back region;

a plurality of abdominal muscle support pads that are configured to engage one another to form a unitary abdominal muscle support structure that generally conforms with and supports a wearer's abdominal muscle region;

an inner, elastic belt, which engages said back support pad, arranges to extend around the sides of said torso, and engages said unitary abdominal muscle support structure, so as to elastically support said unitary abdominal muscle support structure in spaced apart relationship to said back support pad, thereby forming a compound torso support structure that supports said wearer's abdominal muscle region and said wearer's lower back region; and an outer belt, which engages said back support pad, extends therefrom outside of said inner, elastic belt, and engages said plurality of abdominal muscle support pads, said outer belt being arranged to tighten said abdominal muscle support structure and said back support pad of said compound torso support structure about the torso of the wearer independently of said inner, elastic belt, causing a reduction in tension of said inner, elastic belt, while maintaining said abdominal muscle support structure supporting said wearer's abdominal muscle region and said back support pad supporting said wearer's lower back region.

20. A torso support apparatus according to claim 19, wherein each of said abdominal muscle support pads has a first opening therein, through which a respective looped portion of said inner, elastic belt passes, and wherein said back support pad has a pair of first openings therein, through which respective portions of said inner, elastic belt that extend to looped portions thereof pass, for attaching said plurality of abdominal muscle support pads in spaced apart relationship to said back support pad, and wherein said inner, elastic belt has first and second ends, which pass through respective ones of said pair of first openings in said back support pad, and are joined together to form a continuous inner, elastic loop belt that attaches said plurality of abdominal muscle support pads in spaced apart relationship to said back support pad.

21. A torso support apparatus according to claim 20, wherein said back support pad has a pair of second openings therein, each of said abdominal support pads has a second opening therein, and wherein said outer belt passes through said first and second openings in said back support pad and said first and second openings in said abdominal muscle support pads in such a manner as to tighten said plurality of abdominal muscle support pads and said back support pad about the torso of the wearer.

22. A torso support apparatus according to claim 20, further including a belt loop element through which respective ends of said outer belt, that have passed through said first and second openings in said abdominal muscle support pads, pass and allow said respective ends of said outer belt to be looped back upon and engage portions of said outer belt between said back support pad and said pair of abdominal support pads.

23. A torso support apparatus according to claim 22, wherein said respective ends of said outer belt are configured to be joined to said portions of said outer belt between said back support pad and said pair of abdominal support pads, and wherein said respective ends of said outer belt include fastener elements which are joined to associated fastener elements provided at said portions of said outer belt between said back support pad and said pair of abdominal support pads.

* * * * *